United States Patent [19]

Demozay

[11] 4,132,785

[45] Jan. 2, 1979

[54] ISOPROPYL PARATHION AS AN INSECTICIDE FOR TREATING SOIL

[75] Inventor: Daniel Demozay, Lyons, France

[73] Assignee: Philagro S.A., Lyons, France

[21] Appl. No.: 603,270

[22] Filed: Aug. 11, 1975

[30] Foreign Application Priority Data

Aug. 14, 1974 [FR] France ............................. 74 28780

[51] Int. Cl.$^2$ ............................................ A01N 9/36
[52] U.S. Cl. .................................................. 424/218
[58] Field of Search ......................................... 424/218

[56] References Cited

U.S. PATENT DOCUMENTS

3,639,593  2/1972  Garrison ............................. 424/218

OTHER PUBLICATIONS

Plapp et al., "J. Econ. Ent.", vol. 58, No. 5, (1965), pp. 953-956.
Metcalf et al., "J. Econ. Ent.", vol. 42, No. 5, (1949), pp. 721-728.

*Primary Examiner*—V. D. Turner
*Attorney, Agent, or Firm*—Browdy and Neimark

[57] ABSTRACT

Insecticide compositions suitable for the treatment of soil. They contain 0,0-diisopropyl-0-p.nitrophenol thionophosphate as active material.

Compositions suitable for controlling animal parasites in agriculture or market-gardening.

4 Claims, No Drawings

ISOPROPYL PARATHION AS AN INSECTICIDE FOR TREATING SOIL

FIELD OF THE INVENTION

The present invention relates to the control of animal parasites inhabiting the soil and, more particularly, to insecticide compositions and a method of applying same particularly suitable for the killing of larva and adult insects in the ground.

BACKGROUND OF THE INVENTION

Numerous insects spend all or part of their life in the soil. Insects of this kind are known to cause serious damage to crops because they attack either seeds planted in the soil or already developed roots.

These parasites include a certain number of diptera, such as flies:
  crucifer flies (*Hylemyia brassicae, Chortophila floralis*)
  the carrot fly (*Psila rosae*)
  the onion fly (*Hylemyia antiqua*)
  the seedling fly (*Hylemyia cilicrura* or *Phorbia platura*)
  the grey corn fly (*Leptohylemyia coarctata*)
  the frit fly (*Oscinella Frit*)
  the rice fly (*Hydrelia* spp.)
  the asparagus fly (*Platyparea poeciloptera*)
  the endive fly (*Ophiomyia pinguis*)
and flies which pupate in the soil, such as cecidomyiae and trypetidae. Parasitic diptera of the type in question also include crane flies and bibios (*Bibio hortulanus*). Soil parasites of the type in question also include coleoptera, such as elaters or elateridae (*Agriotes* spp.), cockchafer grubs (*Melolontha* spp., *Aphodus* and *Heteronychus arator, Costelytra zealandica*) and oryctae, symphiles such as *Scutigerella* sp., myriapoda such as *Blaniulus* sp. and mole crickets, such as *Gryllotalpa gryllotalpa*.

The control of all the above-mentioned parasites, known as soil parasites, involves serious problems in agriculture on account of the need to find products which are persistent enough in their effect to remain active for several months. The most widely used insecticides for this type of application have long been the so-called "chlorinated" insecticides such as DDT, Endrin, Dieldrin, Aldrin, chlordane, hexachlorocyclohexane, whose effect against parasites of this type is remarkable.

Unfortunately, insecticides of this kind generally have high toxicity levels and, above all, excessive stability which results in the presence of residues over prolonged periods of time which in turn results in the appearance of extremely troublesome cumulative phenomena. These phenomena and pollution control measures have prompted numerous countries, including the USA, to introduce partial or complete bans on the use of many of these compounds, thus depriving farmers and horticulturists of means of controlling many ground insects.

SUMMARY

Accordingly, there is a need to find and perfect new insecticides which, on the one hand, are persistent enough in their effect to remain active for a sufficiently long period but which, on the other hand, are degraded after a certain time to prevent any cumulative phenomena and which are preferably as non-toxic as possible.

It has now surprisingly been found that O,O-diisopropyl-O-p.nitrophenol thionophosphate corresponding to the formula

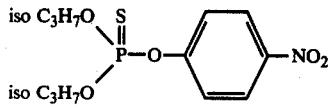

hereinafter referred to in short as iso-P.P., has particularly remarkable properties of the type mentioned above, for application to the soil for the control of soil containing insects.

Accordingly, the invention relates to a method of controlling soil parasites, particularly soil insects, in which the parasites are treated with a biologically active quantity of iso-P.P.

The invention also relates to parasiticide compositions intended for controlling soil parasites, particularly soil insects, and containing iso-P.P. as the active material.

DETAILED DESCRIPTION OF EMBODIMENTS

Iso-P.P. has long been known as a mediocre insecticide which, in particular, has a considerably weaker activity than its lower homologues, methyl parathion and ethyl parathion, which are two commercial insecticides of considerable importance throughout the world. All the studies which have been carried out on iso-P.P. were conducted after METCALF and MARCH (Journal of Economic Entomology No. 42, pages 721–728 and No. 43, pages 630–637) had shown that iso-P.P. had a much lower toxicity in bees than in domestic flies, which presented it with considerable potential interest as an agricultural insecticide.

However, all the studies subsequently carried out on this product showed that it was much less active generally than parathion, cf. in particular Journal of Economic Entomology, Vol. 65, pages 1295–1298, Vol. 65, No. 5, pages 1481–1482 (action on heliotis), Vol. 58, No. 5, pages 953–956 (action on domestic flies and mosquitoes), Vol. 47, pages 507–514 (action on melon flies, *Dacus cucurbitae*, fruit flies, *Ceratitis capitata*). Since this difference in activity was of the order of 10 to 100 in favor of ethyl parathion, any possible development of iso-P.P. appeared out of the question, in spite of the low toxicity of this compound in warm-blooded animals.

However, it has now unexpectedly been found that iso-P.O. has a remarkable pesticidal activity on soil parasites, particularly soil insects, which is much greater than that of parathion used under the same conditions. This discovery is completely opposite to what had been assumed from the prior art. In these tests, iso-P.P. shows an acitivity substantially identical with that of other phosphoric esters which have recently been proposed for controlling soil parasites, such as chlormephos (O,O-diethyl-S-chloromethyl dithiophosphate), fonophos (O-ethyoxy-S-phenyl ethyl thio-phosphonate) or chlorpyrifos (O,O-diethyl-O-trichloro-2,4,5-pyridine thionophosphate).

The remarkable insecticidal properties of iso-P.P. in controlling soil insects were demonstrated in particular by the following standard test for determining effectiveness of soil insecticides from which the results obtained show that it is highly suitable against various soil flies which attack crops.

Soil which has not previously been subjected to any insecticidal treatment is treated with the products to be tested used in the various doses indicated below. Soil samples are taken at regular intervals and about 50 larvae of *Musca domestica* ready for pupation are placed on the samples. After the adults have hatched (if hatching occurs), the number of larvae which have not hatched are counted to determine the percentage mortality.

The results obtained are set out in Table I below:

Table 1

| Product | Dose kg/ha | Percentage mortality after "n" days | | | | |
|---|---|---|---|---|---|---|
| | | n = 1 | n = 20 | n = 30 | n = 60 | n = 90 |
| Iso-P.P., product according to the invention | 5 | 100 | 100 | 100 | 100 | 100 |
| | 2.5 | 100 | 100 | 100 | 100 | 100 |
| Parathion | 5 | 80 | 10 | 0 | 0 | 0 |
| | 2.5 | 70 | 5 | 0 | 0 | 0 |
| Chlormephos | 5 | 100 | 100 | 100 | 98 | 88 |
| | 2.5 | 100 | 100 | 100 | 90 | 80 |
| Fonophos | 5 | 100 | 100 | 100 | 100 | 100 |
| | 2.5 | 100 | 100 | 100 | 100 | 100 |
| Chlorpyrifos | 5 | 100 | 95 | 90 | 85 | 75 |
| | 2.5 | 100 | 92 | 85 | 80 | 20 |

It can be seen from these results that the product according to the invention has a remarkable activity which remains complete after 3 months, even in the low dose. This is all the more surprising insofar as comparison of these results with those obtained with parathion, which, chemically, is not very different from iso-P.P., shows that iso-P.P. is vastly more active than parathion in its immediate effect and infinitely more active in its persistence. This is entirely unexpected because all the indications of the prior art, confirmed by the tests carried out by applicants on various other parasites, were that exactly the opposite results should have been obtained.

The results of these tests on various parasites are set out in the following Table which indicates the lethal doses 50 (LD 50) approached expressed in ppm. for direct application of the insecticides to the insects.

Table 2

| | Iso-P.P. | Parathion |
|---|---|---|
| *Aedes aegypti* (larvae) | 0.1–1 | 0.001–0.005 |
| *Musca domestica* (adult) | 400 | 10–50 |
| *Sitophilus granarius* (adult) | 3000 | 5–50 |
| *Tenebrio molitor* (larvae) | >10,000 | 200 |
| *Anagasta kuehniella* (larvae) | 2.5 | 0.1–0.5 |
| *Spodoptera littoralis* (larvae) | >10,000 | 200 |
| *Blatella germanica* (adult) | 60 | 5–10 |

It can be seen from Table 1 that the results obtained with iso-P.P. are at least equivalent to those obtained with the phosphorus-based compounds commercially used for this type of application. By contrast, iso-P.P. is distinguished from these compounds by its very much lower toxicity in warm-blooded animals. The toxicities of these compounds (as measured by the acute LD 50 by the oral route in rats) are as follows:

Iso-P.P. (Product according to the invention) = 537 mg/kg

Chlorpyrifos = 163 mg/kg

Fonofos = 10 mg/kg

Chlormephos = 7 mg/kg

Parathion = 13 mg/kg

Accordingly, it can be seen that the toxicity of iso-P.P. is more than three times lower than that of chlorpyrifos, to which it is greatly superior for the application according to the invention, and more than 50 times lower than that of fonofos and chlormephos which give comparative results. This is, accordingly, a considerable advantage from the point of view of safety of use and protection of the environment.

In addition, this low toxicity enables the product according to the invention to be used by amateur gardeners in whose case only substantially non-toxic products can be safely used.

Moreover iso-P.P. as all the phosphorous derivatives has a chemical stability rather limited when it is in contact with plant or soil.

The molecules break themselves in two moieties with formation of p.nitrophenol: this avoids the accumulation of residues of the basic toxic compound.

Another considerable advantage of iso-P.P. is the almost complete absence of phytotoxicity with respect to cultures. In this respect, it is distinguished very clearly from parathion as shown by the following Table which gives the phytotoxicities obtained under glass with granules containing 5% of active material on various cultures and in various doses.

The figures appearing in the Table correspond to the rates of application and are given in Kg/Ha.

Table 3

| | Iso-P.P. | | | Parathion | | |
|---|---|---|---|---|---|---|
| | 1 | 2.5 | 5 | 1 | 2.5 | 5 |
| Wheat | 0 | 0 | 0 | X | XX | XX |
| Carrots | 0 | X | X | X | XX | XX/ |
| Beans | 0 | 0 | 0 | X | XX | XX/ |
| Beetroot | 0 | 0 | / | / | XX | XXX |
| Gherkins | 0 | / | / | / | / | XX/ |

/ very slight phytotoxicity
X slight phytotoxicity acceptable in practice
XX distinct phytotoxicity probably unacceptable in practice
XXX very pronounced phytotoxicity destroying most of the plants.

For its use in practice for controlling soil parasites, the compound according to the invention is generally formulated by the methods commonly used in the pesticide industry, i.e. in association with fillers and/or various additives intended to facilitate its action on the parasites and its use by the consumer. The formulations may be solid or liquid and may be used as such or may be diluted with water before use.

Solid formulations used as such include powders for application as such comprising the active material and an inert filler such as talcum, kaolin, fuller's earth and other inert fillers of the type normally used. The iso-P.P. is best used in this form when it is employed for treating seedlings before they are planted in soil.

The iso-P.P. may also be formulated as granules generally containing from 1 to 20% of active material and either impregnated in or applied by coating to a central core of suitable size. This type of formulation is widely used for this type of application.

Solid formulations intended for dilution with water include wettable powders which normally contain from 20 to 95% of active material, from 0 to 5% of a wetting agent, from 3 to 10% of a dispersant and, where necessary, from 0 to 10% of a stabilizer and other additives, such as penetration agents, adhesives, anti lumping agents, solvents, etc.

For example, a wettable powder may have the following composition:

| | |
|---|---|
| Iso-P.P. | 50 % |
| calcium lignosulphate (deflocculant) | 5 % |
| anionic wetting agent : sodium alkyl | |

| -continued | |
|---|---|
| naphtalene sulfonate sold by Rhone-Poulenc under Trademark "Emogil" | 1 % |
| antilumping silica, sold by Rhone-Poulenc under Trademark "Zeosil" | 5 % |
| kaolin (filler) | 39 % |

It is also possible to use aqueous dispersions and emulsions obtained by diluting in water a wettable powder or an emulsifiable concentrate obtained by diluting the active material with a suitable organic solvent additionally containing a surfactant.

Example of these formulations and of different additives which may be used in mixture with active materials may be found in the book "Pesticide Formulation" of Wade Van Valkenburg, edited by Marcel Dekker Inc. N.Y. 1973. See namely chap. 5, pp. 143 to 188. Formulation of Pesticidal Dusts, Wettable Powders and Granules.

For each of these formulations, the iso-P.P. may be used either on its own or in admixture with other pesticides, more especially insecticides, nematicides, fungicides or herbicides, intended to extend or strengthen its range of activity. Suitable complementary pesticides of this type include phosphorus-based insecticides such as chlormephos, chlorpyrifos, trichloronate, carbamates such as aldicarb, chlorine-containing insecticides such as lindane.

They may also be used in admixture with nematicides such as aldicarb, thionazin, etc., and with fungicides, especially fungicides active against soil fungi or fungi affecting seedlings, such as benomyl, manebe, etc.

The doses in which the iso-P.P. is used may vary according to the conditions of use and according to the type and virulence of the parasites. In general, doses of from 0.5 to 20 kg/ha of active material are suitable, the preferred doses amount to between 2 and 10 kg/ha.

It will be obvious to those skilled in the art that various changes may be made without departing from the scope of the invention and the invention is not to be considered limited to what is described in the specification.

What is claimed is:

1. A method of treating soil to destroy soil insects selected from the group consisting of *Musca domestica, Hylemyia brassicae, Chortophila floralis, Psila rosae, Hylenyia antiqua, Hylemyia cilicrura, Phorbia platura, Leptohylemyia coarctata, Oscinella Frit, Hydrelia* spp., *Platyparea poeciloptera, Ophiomyia pinguis,* cecidomyia, trypetida, crane fly, *Bibio hortulanus,* agriotes spp., *Melolontha* spp., *Aphodus, Heteronychus arator, Costelytra realandica,* orycta, *Scutigerella* sp., *Blaniulus* sp. and *Gryllotalpa gryllotalpa* residing in the soil, comprising
   applying to the soil an insecticidally effective amount of O,O-diisopropyl-O-p.nitrophenyl thionophospate corresponding to the formula

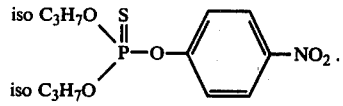

2. The method of claim 1, wherein the rate of application is between 2 and 10 kgs/ha.

3. The method of claim 1, wherein the active material is applied in the form of a granulate.

4. A method of protecting seedlings from soil insects selected from the group consisting of *Musca domestica, Hylemyia brassicae, Chortophila floralis, Psila rosae, Hylenyia antiqua, Hylemyia cilicrura, Phorbia platura, Leptohylemyia coarctata, Oscinella Frit, Hydrelia* spp., *Platyparea poeciloptera, Ophiomyia pinguis,* cecidomyia, trypetida, crane fly, *Bibio hortulanus,* agriotes spp., *Melolontha* spp., *Aphodus, Heteronychus arator, Costelytra realandica,* orycta, *Scutigerella* sp., *Blaniulus* sp. and *Gryllotalpa gryllotalpa* residing in the soil by treating said seedlings prior to the permanent planting therein, comprising:
   applying to the seedlings an insecticidally effective amount of the active compound O,O-diisopropyl-O-p.nitrophenyl thionophosphate corresponding to the formula

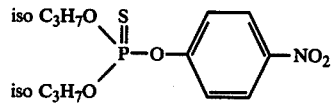

before planting said seedlings; and
   planting said seedlings having said active compound applied thereto to bring said active compound into contact with the soil.

* * * * *